US007922746B2

(12) United States Patent
Miller

(10) Patent No.: US 7,922,746 B2
(45) Date of Patent: Apr. 12, 2011

(54) SPINAL ROD EXTENDERS AND METHODS OF USE

(75) Inventor: Keith Miller, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 657 days.

(21) Appl. No.: 11/469,008

(22) Filed: Aug. 31, 2006

(65) Prior Publication Data
US 2008/0086126 A1 Apr. 10, 2008

(51) Int. Cl.
A61B 17/70 (2006.01)
(52) U.S. Cl. ........................................ 606/250; 606/252
(58) Field of Classification Search .................. 606/259, 606/260, 278, 54, 59, 250–253; 403/385, 403/391, 393; 248/229.25
See application file for complete search history.

(56) References Cited

U.S. PATENT DOCUMENTS

| 1,201,864 | A | * | 10/1916 | Overmeyer | 606/54 |
| 2,767,003 | A | * | 10/1956 | Gilmont | 403/385 |
| 2,970,798 | A | * | 2/1961 | Friotchle et al. | 248/229.25 |
| 3,154,331 | A | * | 10/1964 | Engelhardt | 403/385 |
| 4,733,657 | A | | 3/1988 | Kluger | |
| 4,771,767 | A | * | 9/1988 | Steffee | 606/256 |
| 4,957,495 | A | | 9/1990 | Kluger | |
| 5,196,013 | A | | 3/1993 | Harms et al. | |
| 5,261,907 | A | | 11/1993 | Vignaud et al. | |
| 5,330,473 | A | | 7/1994 | Howland | |
| 5,374,267 | A | * | 12/1994 | Siegal | 606/250 |
| 5,437,671 | A | | 8/1995 | Lozier et al. | |
| 5,474,551 | A | | 12/1995 | Finn et al. | |
| 5,478,340 | A | | 12/1995 | Kluger | |
| 5,498,262 | A | | 3/1996 | Bryan | |
| 5,624,442 | A | | 4/1997 | Mellinger et al. | |
| 5,645,544 | A | | 7/1997 | Tai et al. | |
| 5,669,910 | A | * | 9/1997 | Korhonen et al. | 606/252 |
| 6,217,578 | B1 | | 4/2001 | Crozet et al. | |
| 6,238,396 | B1 | | 5/2001 | Lombardo | |
| 6,368,320 | B1 | | 4/2002 | Le Couedic et al. | |

(Continued)

FOREIGN PATENT DOCUMENTS
FR 2 795 622 1/2001
(Continued)

OTHER PUBLICATIONS

"International Search Report," International Application No. PCT/US2007/077060, Jan. 15, 2008, European Patent Office, Rijswijk, Netherlands.

Primary Examiner — Thomas C Barrett
Assistant Examiner — Nicholas Woodall

(57) ABSTRACT

A spinal rod assembly may be formed by attaching an extension portion onto a spinal rod that extends along a longitudinal axis. The extension portion may include a rod coupler that attaches to the spinal rod with a first coupling that includes a first degree of rotational freedom and a first degree of translational freedom in positioning the rod coupler relative to the spinal rod along the longitudinal axis. The extension portion may further include an extender rod including an elongated rod body that may be secured to the rod coupler using a second coupling that includes at least a second degree of rotational freedom in positioning the extender rod relative to the rod coupler about an axis substantially perpendicular to the longitudinal axis. The extension portion may be assembled in situ to a spinal rod that has been previously secured to vertebral bodies in a patient.

14 Claims, 6 Drawing Sheets

U.S. PATENT DOCUMENTS

| | | |
|---|---|---|
| 6,402,749 B1 | 6/2002 | Ashman |
| 6,524,310 B1 | 2/2003 | Lombardo et al. |
| 6,551,318 B1 | 4/2003 | Stahurski |
| 6,685,705 B1 | 2/2004 | Taylor |
| 6,736,817 B2 | 5/2004 | Troxell et al. |
| 6,755,830 B2 | 6/2004 | Minfelde et al. |
| 6,802,844 B2 | 10/2004 | Ferree |
| 6,872,208 B1 | 3/2005 | McBride et al. |
| 6,887,241 B1 | 5/2005 | McBride et al. |
| 2002/0143330 A1 | 10/2002 | Shluzas |
| 2003/0032959 A1 | 2/2003 | Yeh |
| 2003/0045874 A1* | 3/2003 | Thomas, Jr. .................. 606/61 |
| 2005/0113927 A1 | 5/2005 | Malek |
| 2005/0228378 A1* | 10/2005 | Kalfas et al. .................. 606/61 |
| 2005/0234449 A1 | 10/2005 | Aferzon |
| 2005/0277926 A1 | 12/2005 | Farris |
| 2005/0277932 A1 | 12/2005 | Farris |
| 2006/0009767 A1 | 1/2006 | Kiester |

FOREIGN PATENT DOCUMENTS

| | | |
|---|---|---|
| WO | 0230307 | 4/2002 |
| WO | 2004039268 | 5/2004 |
| WO | 2005099603 | 10/2005 |
| WO | 2005122930 | 12/2005 |

\* cited by examiner

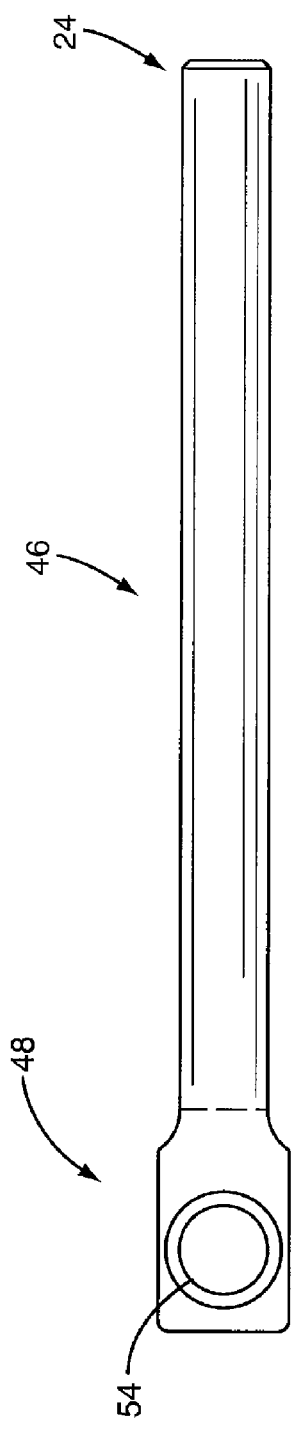
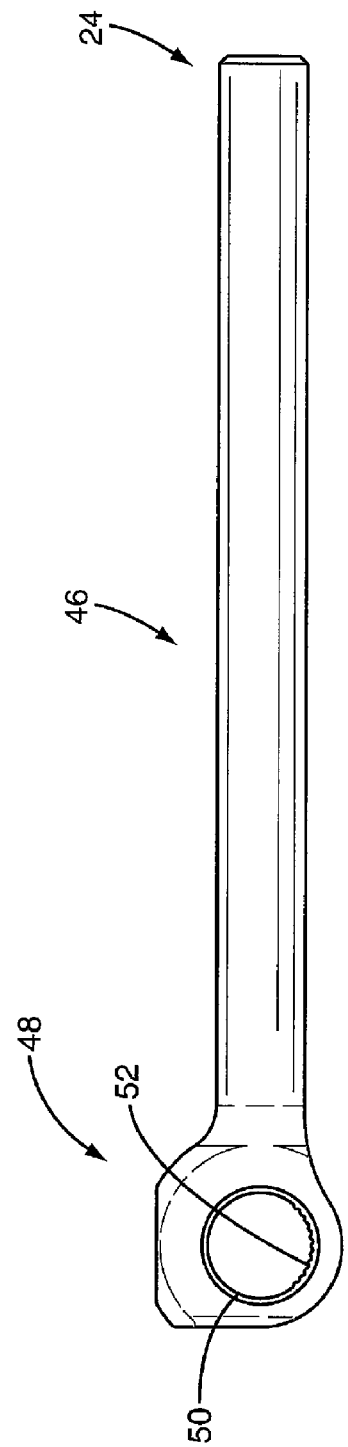
FIG. 7
FIG. 8

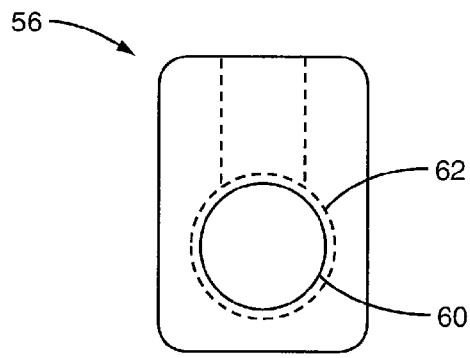
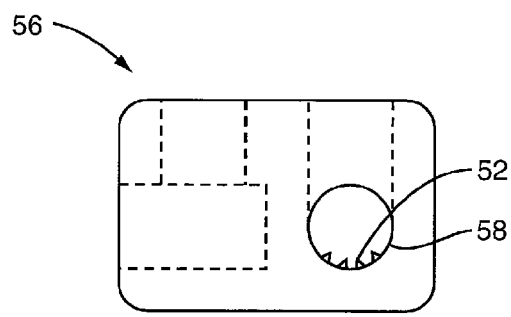
FIG. 11  FIG. 12
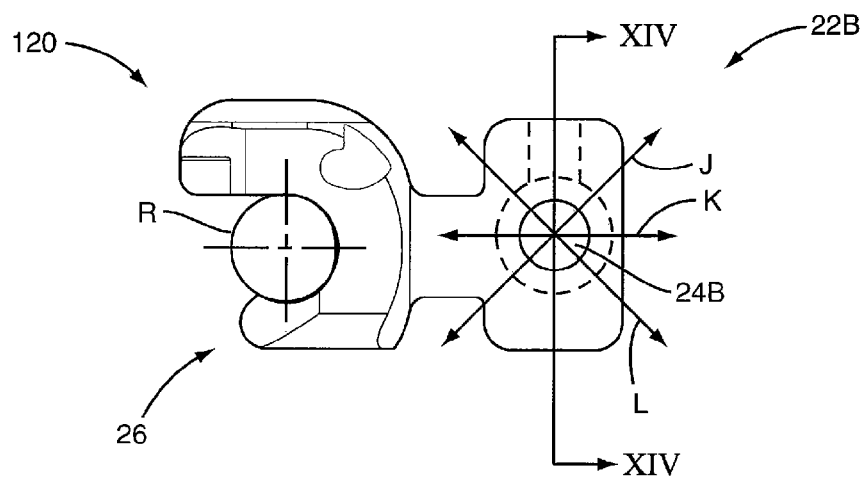
FIG. 13
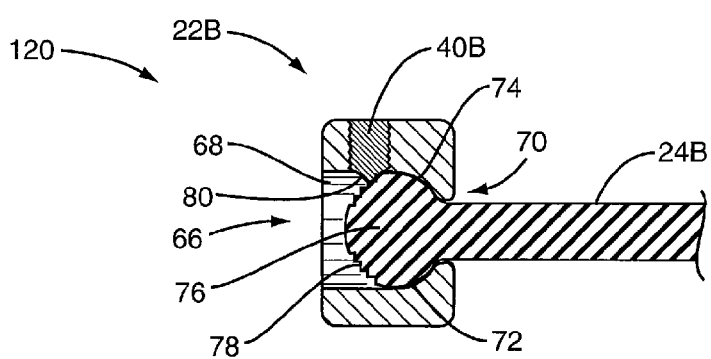
FIG. 14

SPINAL ROD EXTENDERS AND METHODS OF USE

BACKGROUND

Spinal rods are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between vertebral bodies. For either type of surgical treatment, spinal rods may be attached to the exterior of two or more vertebrae, whether it is at a posterior, anterior, or lateral side of the vertebrae. In other embodiments, spinal rods are attached to the vertebrae without the use of dynamic implants or spinal fusion.

Spinal rods may provide a stable, rigid column that encourages bones to fuse after spinal-fusion surgery. Further, the rods may redirect stresses over a wider area away from a damaged or defective region. Also, a rigid rod may restore the spine to its proper alignment. In some cases, a flexible rod may be appropriate. Flexible rods may provide some advantages over rigid rods, such as increasing loading on interbody constructs, decreasing stress transfer to adjacent vertebral elements while bone-graft healing takes place, and generally balancing strength with flexibility.

It is sometimes the case, such as with degenerative diseases, that vertebral levels adjacent to a previously implanted spinal rod may begin to deteriorate. In other cases, such as with spinal correction, a surgeon may elect to insert spinal rods in stages. In either case, revision surgeries may be indicated to secure additional vertebral levels with longer spinal rods. These types of surgeries usually require detachment and removal of the originally implanted rods and insertion of a longer rod into the existing anchors. However, a surgeon may prefer to leave the original implant intact to preserve fusion sites and/or implant geometry. Accordingly, conventional spinal rod systems may not permit extendable attachment of additional spinal rods to previously implanted spinal rods.

SUMMARY

Illustrative embodiments disclosed herein are directed to a spinal rod assembly that may be formed by attaching an extension portion onto a spinal rod that extends along a longitudinal axis. The extension portion may be assembled in situ to a spinal rod that has been previously secured to vertebral bodies in a patient. The extension portion may be assembled to a spinal rod prior to insertion into a patient. For either approach, the extension portion may include a rod coupler that attaches to the spinal rod with a first coupling that includes a first degree of rotational freedom and a first degree of translational freedom in positioning the rod coupler relative to the spinal rod along the longitudinal axis. The rod coupler may include an open channel formed between first and second walls, the channel sized to accept the spinal rod in a lateral direction between the first and second walls. One or both of the walls may include a retainer extending into the channel. The rod coupler may be positioned as desired relative to the spinal rod and secured. The extension portion may further include an extender rod including an elongated rod body that may be secured to the rod coupler using a second coupling that includes at least a second degree of rotational freedom in positioning the extender rod relative to the rod coupler about an axis substantially perpendicular to the longitudinal axis. In one embodiment, the second coupling includes a second degree of translational freedom in establishing an offset of the rod extension relative to the spinal rod.

BRIEF DESCRIPTION OF THE DRAWINGS

FIG. 7 is a top view of an extender rod according to one embodiment;

FIG. 8 is a perspective view of an extender rod according to one embodiment;

FIG. 11 is a front view of a spinal rod extender coupling block according to one embodiment;

FIG. 12 is a side view of a spinal rod extender coupling block according to one embodiment;

FIG. 13 is an axial view of a spinal rod extender assembly according to one embodiment; and FIG. 14 is side section view of a spinal rod extender assembly according to one embodiment.

DETAILED DESCRIPTION

Figure 1:
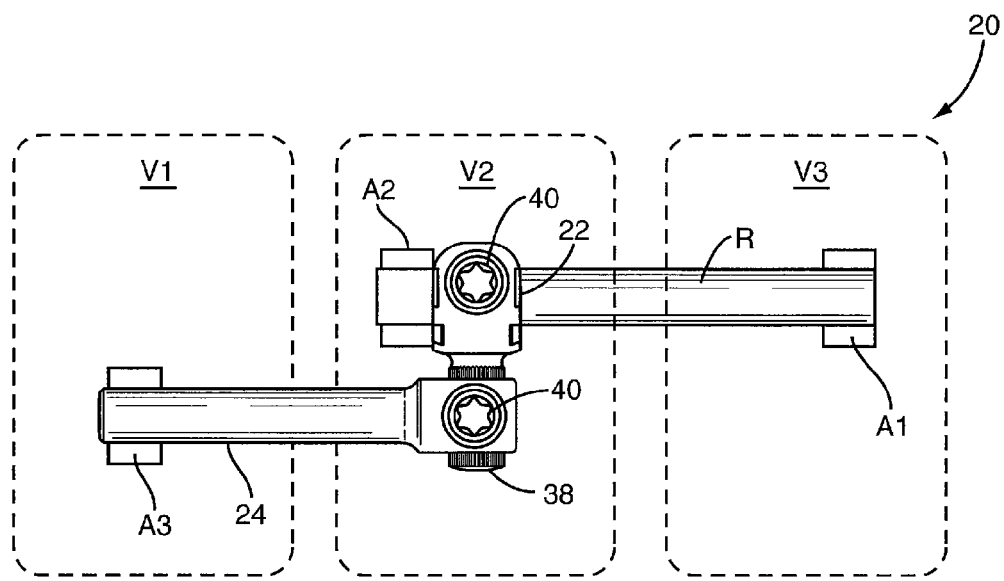
FIG. 1 is a top view of a rod assembly including a rod extender secured to vertebral members according to one embodiment.
Figure 2:
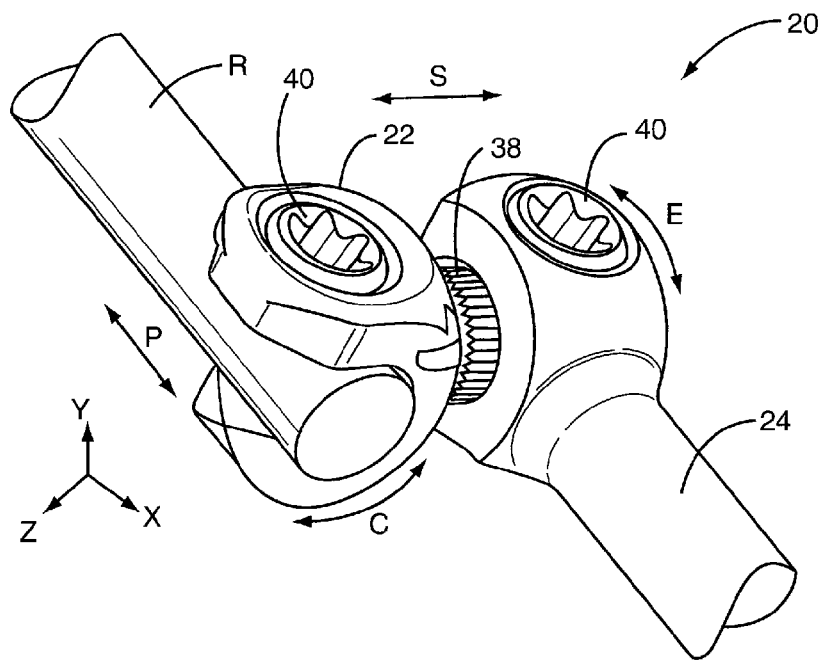
FIG. 2 is a perspective view of a spinal rod extender according to one embodiment.

The various embodiments disclosed herein are directed to spinal rod extenders that permit linking of multiple rod portions, thereby providing an extendable, modular rod system. Generally, the spinal rod extenders may be secured to a conventional rod prior to or after implantation into a patient. A conventional rod may be similar to those used in the CD Horizon® rod systems available from Medtronic, Spinal & Biologics Division in Memphis, Tenn., USA. The rod extenders may be implanted at the same time and in conjunction with a conventional rod. However, the rod extenders also are advantageously attachable to conventional rods that are already secured to vertebral bodies in a patient. Thus, the rod extenders may be implanted at some time after a conventional rod is implanted, such as in a revision procedure. Various embodiments of a spinal rod extender may be implemented in a spinal rod assembly of the type indicated generally by the numeral 20 in FIGS. 1 and 2. Spinal rods assemblies 20 of the type shown may be attached to a spine at various locations, including posterior, lateral, and anterior locations. Spinal rod assemblies 20 may also be attached at various sections of the spine, including the base of the skull and to vertebrae in the cervical, thoracic, lumbar, and sacral regions. The spinal rod assemblies 20 may be secured to the spine using conventionally known attachment anchors A1, A2, A3 such as pedicle screws or other threaded anchors, and other conventionally known hardware, including for example hooks and plates. Accordingly, the spinal rod assemblies 20 may include various lengths, diameters, and configurations. Thus, the illustrations in FIGS. 1 and 2 are provided merely as a representative example of one application of a spinal rod assembly 20. FIG.

1 shows a top view of the spinal rod assembly 20 while FIG. 2 shows a perspective view the spinal rod assembly 20 in which a conventional spinal rod R is attached to extender components, including an extender coupler 22 and an extender rod 24.

In FIG. 1, the spinal rod assembly is shown relative to representative vertebral bodies V1, V2, V3, illustrated simply as dashed blocks. In an exemplary application of the rod assembly 20, the conventional spinal rod R may have been previously implanted into a patient and secured to vertebral bodies V1, V2 using appropriate anchors A1, A2. Various types of anchors, including for example fixed, and multi-axial pedicle screws also available with the CD Horizon® rod system family of devices. At some later point in time, the extender coupler 22 and an extender rod 24 may be added to the existing rod R without having to remove the rod R or detach the anchors A1, A2. Instead, the rod coupler 22 and extender rod 24 are attached to the rod R in situ and the extender rod 24 may be secured to a third vertebral body V3 using a third anchor A3. In an alternative approach, the entire rod assembly 20 may be assembled and secured to the vertebral bodies V1, V2, V3 at substantially the same time.

The extender coupler 22 and extender rod 24 are generally constructed of biocompatible materials. These include metals such as stainless steels, cobalt-chrome, titanium, and shape memory alloys such as nitinol. Non-metallic components, including polymers made from materials such as PEEK and UHMWPE, are also contemplated. Those skilled in the art will comprehend various advantage and characteristics provided by different material choices. Through appropriate material choices, substantially rigid constructs or semi-rigid or flexible constructs may be created.

Figure 3:
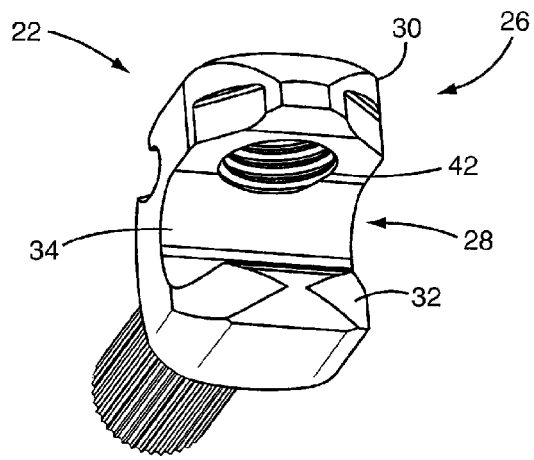
FIG. 3 is a perspective view of a spinal rod extender coupler according to one embodiment.
Figure 4:
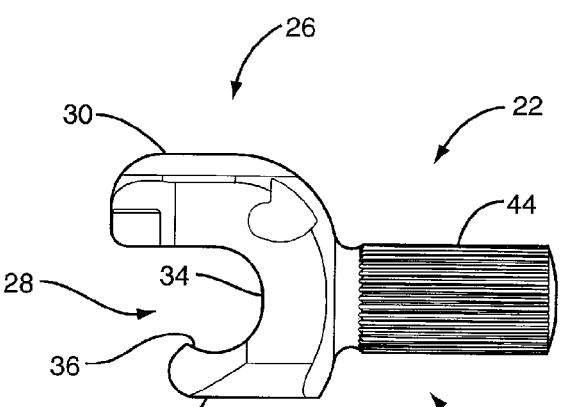
FIG. 4 is a side view of a spinal rod extender coupler according to one embodiment.
Figure 5:
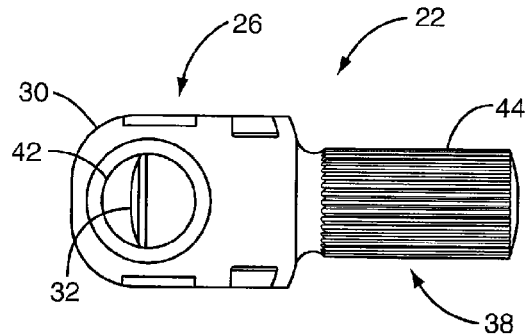
FIG. 5 is a top view of a spinal rod extender coupler according to one embodiment.

A conventional spinal rod R generally includes an elongated body with a circular cross section. However, in the embodiments disclosed herein, non-circular cross sections are equally applicable. Cross section widths between about 3 mm and about 8 mm are known, though other sizes may be used. Regardless of the rod R geometry, the extender coupler 22 includes a receiver section 26 that is configured to accept a rod R. One embodiment of an extender coupler 22 is shown in greater detail in the perspective view provided in FIG. 3. FIG. 4 shows a side view of this same extender coupler 22. FIG. 5 shows a top view of this same extender coupler 22.

In the illustrated embodiment, the receiver section 26 includes a channel 28 that is sized to accept a rod R. The channel 28 is formed between an upper wall 30 and a lower wall 32 and a seating surface 34 extending therebetween. In one embodiment, the upper wall 30 is longer than the lower wall 32. In another embodiment, the upper and lower walls 30, 32 include substantially similar lengths. Similarly, the lower wall 32 may be longer than the upper wall 30. In any event, the lower wall 32 may include a retention feature 36 to retain a rod R that is inserted into the channel 28. The retention feature 36 is formed as a protrusion that extends slightly into the channel 28 towards the upper wall 30. Once a rod R is secured in the channel 28, the retention feature 36 prevents the rod R from dislocating laterally out of the channel 28. Further, in the embodiment shown, the channel 28 is open laterally, with a coupler post 38 extending laterally in a direction opposite the open end of the channel 28. In one embodiment, the channel 28 may be open towards the top or bottom of the extender coupler 22. There is no express requirement that the channel 28 and coupler post 38 extend laterally in opposite directions.

Figure 6:
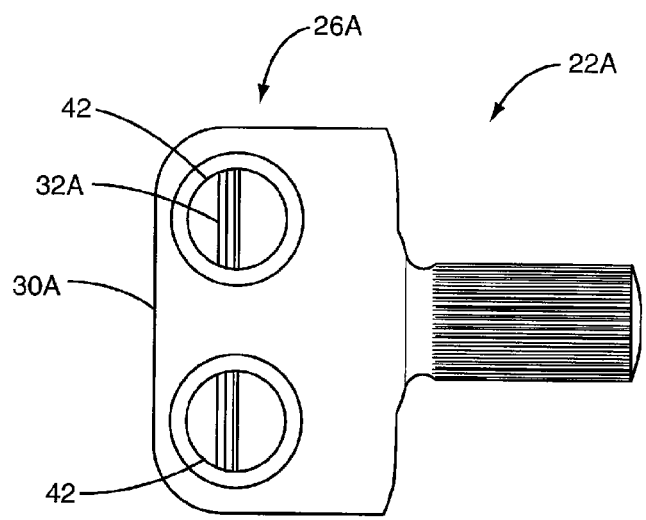
FIG. 6 is a top view of a spinal rod extender coupler according to one embodiment.

A rod R may be secured within the channel 28 with a retainer 40 as shown in FIGS. 1 and 2. The retainer 40 may be implemented as a setscrew as shown, though other types of fasteners may be used. Exemplary retainers 40 may include pins, plugs, dowels, quarter-turn fasteners, clips, rings, and other fasteners conceivable by those skilled in the art. A setscrew retainer 40 as shown may provide substantial clamping forces to secure a rod R within the channel 28. In the embodiment shown, the setscrew retainer 40 is insertable into a threaded aperture 42 in the upper wall 30 of the receiver section 26. In one embodiment, the receiver section 26 includes a single threaded aperture 42 to receive a setscrew retainer 40. In other embodiments, such as that illustrated in FIG. 6, the receiver section 26 includes multiple threaded apertures 42 to receive multiple setscrew retainers 40 for additional securing to a rod R. The extender coupler 22 can be inserted onto and secured to the rod R by clamping the rod R within the channel 28 using the retainer 40.

FIG. 2 shows that there is some flexibility in attaching the extender coupler 22 to the rod R. Specifically, FIG. 2 shows two sets of arrows labeled C and P, respectively. These arrows are shown relative to an X-Y-Z coordinate system. The rod R is generally aligned with the X-axis. It is generally known that rods R may be bent to conform to a patient anatomy or to achieve a desired spinal alignment. However, for the sake of description and simplicity, the rod R shown in FIGS. 1 and 2 is depicted as extending in a straight line. For a curved rod R, the X-Y-Z coordinate system remains relevant by aligning the X-axis of the coordinate system with the longitudinal axis of the rod R at the point where the extender coupler 22 is attached to the rod R. With either convention, the extender coupler 22 may be positioned at various locations along the longitudinal length of the rod R. This flexibility is identified by the arrows labeled P, which extend along the X-axis or along the rod R axis. In addition, the extender coupler 22 may be positioned at various rotatable orientations identified by the arrows labeled C, which rotate about the X-axis or about the rod R axis. That is, the extender coupler 22 may be rotated and secured at various locations (limited potentially by anatomy) within the Y-Z plane. These arrows represent a single degree of translational freedom and a single degree of rotational freedom in positioning the extender coupler 22 to a rod R.

As indicated, the coupler post 38 extends from the receiver section 26. In one embodiment, the coupler post 38 includes splines 44 extending longitudinally about the exterior surface of the coupler post 38. The extender rod 24 is attachable to the coupler post 38 in the manner illustrated in FIGS. 1 and 2. FIGS. 7 and 8 respectively illustrate top and side views of an extender rod 24 according to one embodiment. The extender rod 24 includes an elongated rod portion 46 that is formed substantially similar to conventional rods R. That is, the rod portion 46 includes a circular cross section with a diameter between about 3 mm and about 8 mm. Of course, different diameters and different materials will have different flexural and torsional rigidities. Those skilled in the art will comprehend suitable diameters to achieve desired rod strengths. In other embodiments, the rod portion 46 may include non-circular and even asymmetric cross sections.

The extender rod 24 includes an attachment portion 48 that is disposed at one end of the extender rod 24 in the embodiment shown. In the embodiment shown, the attachment portion 48 is enlarged compared to the rod portion 46. However, depending on the size of the rod portion 46 and the coupler post 38, the attachment portion 48 may include a similar size and width as the rod portion 46. The attachment portion 48 includes an aperture 50 that engages the coupler post 38 of the extender coupler 22. That is, the aperture 50 is sized to receive the coupler post 38. The aperture 50 may extend through the attachment portion 48 or may extend a predetermined depth.

The aperture 50 may include one or more protrusions 52, including for example a plurality of splines, that engage correspondingly-configured splines 44 on the coupler post 38. The aperture 50 may include a slightly larger width than that of the coupler post 38. In this manner, the coupler post 38 may be rotated (as shown by the arrows labeled E in FIG. 2) within the aperture 50 to achieve a desired orientation. Further, the extender rod 24 may be secured at varying offset distances from the rod R as indicated by the arrow S. The amount of adjustment in this offset direction S is limited by the length of the coupler post 38.

Thus, combined with the permissible motion depicted by arrows P and C in FIG. 2, the extender rod system 20 permits two-degrees of rotational freedom and two-degrees of translational freedom in assembling the rod extender components 22, 24 to the rod R. Then, the coupler post 38 may be secured within the aperture 50 with a retainer 40 as shown in FIGS. 1 and 2. As suggested above, the retainer 40 may be implemented as a setscrew as shown, though other types of fasteners may be used. Exemplary retainers 40 may include pins, plugs, dowels, quarter-turn fasteners, clips, rings, and other fasteners conceivable by those skilled in the art. A setscrew retainer 40 as shown may provide substantial clamping forces to secure the coupler post 38 within the aperture 50. Furthermore, the splines 44, 52 cooperate to prevent rotation of the extender rod 24 relative to the extender coupler 22 after the retainer 40 is inserted. In the embodiment shown, the setscrew retainer 40 is insertable into a threaded aperture 54 in the attachment portion 48. In one embodiment, the attachment portion 48 includes a single threaded aperture 54 to receive a setscrew retainer 40. In other unillustrated embodiments, the attachment portion 48 includes multiple threaded apertures 54 to receive multiple setscrew retainers 40.

Figure 9:
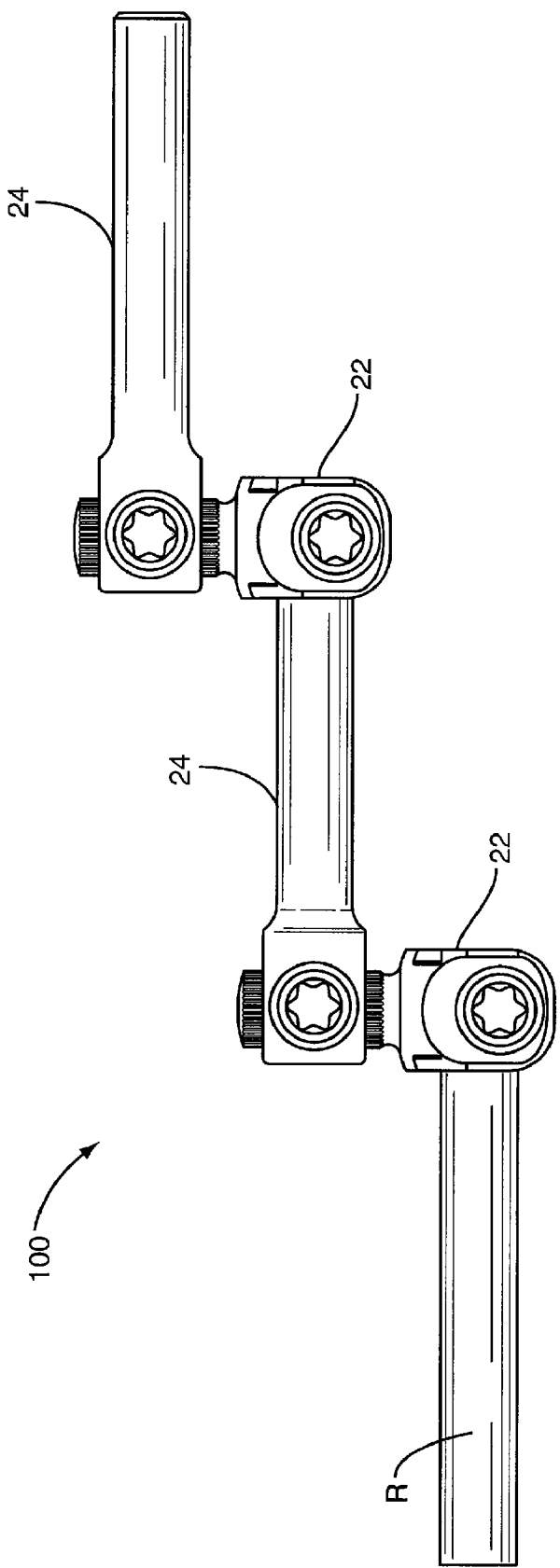
FIG. 9 is a top view of a spinal rod extender according to one embodiment.

FIGS. 1 and 2 depicted a rod assembly 20, including a single extender coupler 22 and a single extender rod 24 coupled to a conventional rod R. Since the extender rod 24 includes a rod portion 46 formed similar to a conventional rod R, a rod system 100 shown in FIG. 9 may be formed using multiple extender couplers 22 and extender rods 24. In the illustrated example, the rod system 100 includes a conventional rod R and a linked rod extender including two extender couplers 22 and two extender rods 24. Additional extender couplers 22 and extender rods 24 may be added as desired to achieve a desired overall length.

Figure 10:
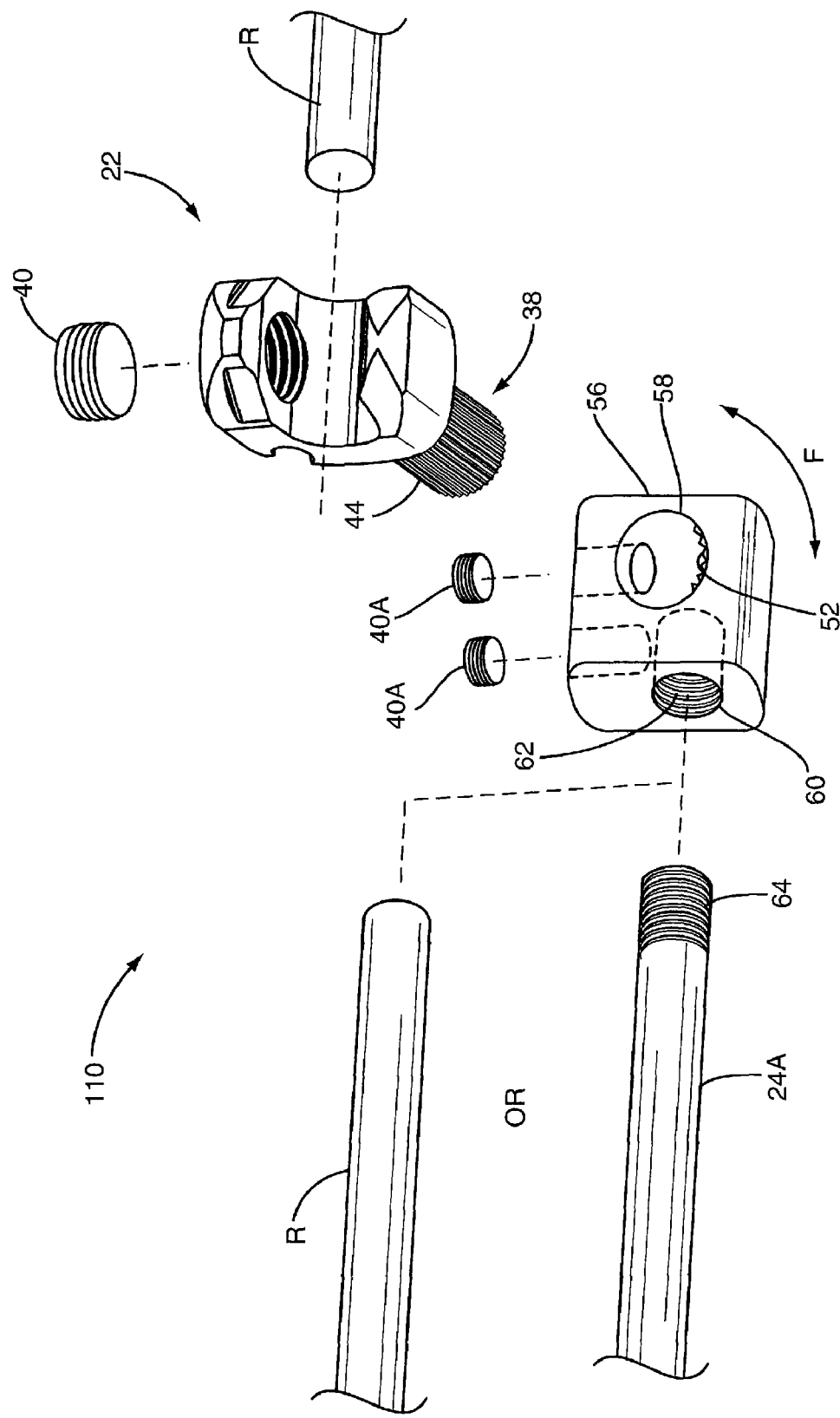
FIG. 10 is a perspective view of an exploded spinal rod extender assembly according to one embodiment.

FIG. 10 depicts an embodiment of a rod extender system 110 that uses an extender coupler 22 for attachment to a conventional rod R as described above. In the present embodiment, an extender rod 24A is attached to the extender coupler 22 via a coupling block 56. Functionally, the coupling block 56 couples the extender rod 24A to the extender coupler 22. Further, the coupling block 56 is rotatable in the direction of arrows F thereby providing flexibility in angling the extender rod 24A relative to the conventional rod R to which the extender coupler 22 is attached. Specific features of the exemplary coupling block 56 are more clearly visible in the front and side views provided in FIGS. 11 and 12. The illustrated coupling block 56 is generally rectangular in form, but other shapes are certainly permissible. For example, elliptical, oblong, or teardrop shapes may be used. The coupling block 56 includes an aperture 58 that engages the coupler post 38 of the extender coupler 22. That is, the aperture 58 is sized to receive the coupler post 38. The aperture 58 may extend through the coupling block 56 or may extend a predetermined depth. The aperture 58 may include one or more protrusions 52, including for example a plurality of splines, that engage correspondingly-configured splines 44 on the coupler post 38. The aperture 58 may include a slightly larger width than that of the coupler post 38. In this manner, the coupler post 38 may be rotated (as shown by the arrows labeled F) within the aperture 58 to achieve a desired orientation. Then, the coupler post 38 may be secured within the aperture 58 with a retainer 40A such as a setscrew or other member as described herein.

The coupling block 56 further includes an aperture 60 that engages the extender rod 24A. That is, the aperture 60 is sized to receive an end of the extender rod 24A. In the embodiment shown, the aperture 60 is oriented to face a direction that is substantially perpendicular to the extender post aperture 58. In other embodiments, the extender rod aperture 60 may face a direction other than substantially perpendicular to the extender post aperture 58. The aperture 60 may extend through the coupling block 56 or may extend a predetermined depth. The aperture 60 may include threads 62 that engage correspondingly-configured threads 64 on the extender rod 24A. Accordingly, the extender rod 24A may be threaded into the aperture 60 in the coupling block 56. Then, the extender rod 24A may be secured using a retainer 40A such as a setscrew or other member as described herein. In an alternative implementation, a conventional rod R may be coupled to the coupling block 56 instead of the illustrated extender rod 24A. The rod R may be inserted into the aperture 60 (which may or may not include threads 62 in the coupling block 56. Then, the rod R may be secured using a retainer 40A such as a setscrew or other member as described herein.

FIGS. 13 and 14 illustrate an embodiment of a rod extender system 120 in which an extender coupler 22B engages an extender rod 24B. The extender coupler 22B includes a receiver section 26 that is configured to accept a rod R as described above. The extender coupler 22B includes an aperture 66 that extends between an enlarged insertion end 68 and a narrowed bottom end 70. Between these ends 68, 70, the aperture 66 includes a spherical surface 72 that is formed to substantially match and engage a spherical surface 74 of an enlarged end 76 of the extender rod 24B. Thus, the spherical surface 74 at the enlarged end 76 of the extender rod 24B and the spherical surface 72 of the aperture 66 form a ball and socket joint that permits poly-axial movement of the extender rod 24B relative to the rod R. The enlarged end 76 of the extender rod 24B may include ridges 78 that can be engaged by a tip 78 of a setscrew retainer 40B. The tip 78 of the setscrew retainer 40B may be pointed as shown. In other embodiments, the tip 78 may be spherical, cupped, conical, or other shapes that would occur to one skilled in the art. Furthermore, the tip 78 may be deformable and include relatively soft materials, including for example metal alloys including silver or polymers including nylon that are deformable to further engage and secure the enlarged end 76 of the extender rod 24B within the aperture 66 in the extender coupler 22B.

The inclusion of a ball-and-socket coupling between the extender rod 24B and the extender coupler 22B provides additional degrees of rotational freedom over previously described embodiments (at the expense of losing the translational freedom identified by the arrow labeled S in FIG. 2). Specifically, the extender rod 24B is able to rotate or pivot about a plurality of axes as represented by the arrows labeled J, K, L in FIG. 13. Notably, these axes are substantially perpendicular to the longitudinal axis of the rod R at the point where the extender coupler 22B is coupled to the rod R.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For example, embodiments described above have contemplated an extender post on an extender coupler that engages an aperture in an extender rod or coupling block. In other embodiments, the post may be disposed on the coupling block or extender rod while the aperture is disposed on the extender coupler. Thus, the coupling block or the extender rod may be inserted into the extender coupler in contrast with the illustrated configurations. The present embodiments are, therefore, to be considered in all respects as illustrative and not restrictive, and all changes coming within the meaning and equivalency range of the appended claims are intended to be embraced therein.

What is claimed is:

1. A spinal rod assembly comprising:
    an elongated rod extending along a first longitudinal axis and including first and second ends and an outer surface extending therebetween;
    a coupler including a first coupling feature and a second coupling feature, the first coupling feature including a receiver section with a channel formed by a back wall and spaced-apart side walls that extend away from the back wall and terminate at ends, the channel having an open side opposite from the back wall and between the ends of the side walls to accept the outer surface of the elongated rod laterally into the receiver section, and the second coupling feature comprising a post extending away from the first coupling feature along a second longitudinal axis substantially perpendicular to the first longitudinal axis; and
    an extender rod including a third coupling feature formed to engage the post of the second coupling feature, and an elongated extender rod body extending from the third coupling feature along a third longitudinal axis,
    the first coupling feature including a first degree of rotational freedom and a first degree of translational freedom in positioning the coupler relative to the first longitudinal axis, and the second and third coupling features cooperating to include at least a second degree of rotational freedom in positioning the extender rod about the second longitudinal axis;
    the post of the second coupling feature sized to fit within an aperture in the third coupling feature such that the post extends across the third longitudinal axis when engaging the aperture; and
    the elongated rod and the elongated extender rod body each having a length to span a plurality of vertebrae.

2. The spinal rod assembly of claim 1 wherein the first and second coupling features are formed into a single coupler member.

3. The spinal rod assembly of claim 1 wherein the second and third coupling features are formed into separate coupler members.

4. The spinal rod assembly of claim 1 wherein one of the side walls includes a retainer extending into the channel.

5. The spinal rod assembly of claim 4 wherein the retainer includes a threaded setscrew.

6. The spinal rod assembly of claim 4 wherein the retainer includes a protrusion extending from the side wall into the channel.

7. The spinal rod assembly of claim 1 wherein the post and the aperture include inter-engaging splines to limit rotation of the post within the aperture when the post is secured within the aperture.

8. The spinal rod assembly of claim 1 wherein the post is formed onto the receiver section of the coupler and the aperture is formed into a separate coupler block that includes a second aperture sized to accept the extender rod.

9. The spinal rod assembly of claim 1 wherein the second and third coupling features cooperate to include at least a second degree of translational freedom in positioning the extender rod relative to the second longitudinal axis.

10. A spinal rod extender system attachable to a spinal rod configured to span a plurality of vertebrae and extending along a first longitudinal axis, the system comprising:
    a coupler including an open channel formed between first and second walls, the channel sized to accept the spinal rod in a lateral direction between the first and second walls, the first wall including a retainer extending into the channel, the coupler further including a post that extends outward away from the channel;
    a block including a first opening that receives the post and a second opening that is aligned transverse to the first opening; and
    an extender rod including an elongated rod body and a coupling feature, said elongated rod body configured to span a plurality of vertebrae and extend along a second longitudinal axis, said coupling feature formed to engage the second opening in a manner that permits rotation of the extender rod about an axis extending transverse to said first longitudinal axis; and
    the first and second openings being aligned such that the second longitudinal axis of the extender rod is positioned to extend through the first opening so that the post extends across the second longitudinal axis when engaging the first opening;
    the first and second openings are isolated from each other within the block.

11. The spinal rod assembly of claim 10 wherein the coupler is formed as a single member.

12. The spinal rod assembly of claim 10 wherein the post and the first opening include inter-engaging splines to limit rotation of the post within the first opening when the post is secured within the first opening.

13. The spinal rod assembly of claim 10 wherein the coupling feature is formed to engage the block in a manner that permits translation of the extender rod along the axis extending transverse to said first longitudinal axis.

14. The spinal rod assembly of claim 10 wherein the first opening extends through the block and the second opening extends a limited distance into the block and includes a back wall.

* * * * *